US011617670B2

(12) United States Patent
Geldart et al.

(10) Patent No.: US 11,617,670 B2
(45) Date of Patent: Apr. 4, 2023

(54) VARIABLE RADIUS SPRING ASSEMBLY

(71) Applicant: GRD INNOVATIONS, LLC, Daytona Beach, FL (US)

(72) Inventors: Michael Geldart, Daytona Beach, FL (US); Alexis Bishop, Orlando, FL (US); Zachary Cronin-Hurley, Orlando, FL (US)

(73) Assignee: GRD Innovations, LLC, Daytona Beach, FL (US)

( * ) Notice: Subject to any disclaimer, the term of this patent is extended or adjusted under 35 U.S.C. 154(b) by 380 days.

(21) Appl. No.: 15/866,618

(22) Filed: Jan. 10, 2018

(65) Prior Publication Data

US 2019/0209358 A1    Jul. 11, 2019

(51) Int. Cl.
*A61F 5/01* (2006.01)

(52) U.S. Cl.
CPC .... *A61F 5/0125* (2013.01); *A61F 2005/0137* (2013.01); *A61F 2005/0179* (2013.01)

(58) Field of Classification Search
CPC .... A61F 5/0125; A61F 5/0102; A61F 5/0106; A61F 5/0585; A61F 2005/0137; A61F 2005/0132; A61F 2005/0179; A61F 5/01; A61F 5/00; A61F 5/02; A61F 5/0123; A61F 2005/0146; A61F 2005/0153; A61F 2005/0165; A61H 1/00; A61H 1/02;
(Continued)

(56) References Cited

U.S. PATENT DOCUMENTS 2,587,166 A * 2/1952 Jovick ............... A61F 5/0125
                                                125/11.17
4,911,709 A * 3/1990 Marlow ............... A61F 2/644
                                                623/39
(Continued)

FOREIGN PATENT DOCUMENTS

WO    WO2016/099896    6/2016

OTHER PUBLICATIONS

Composite Leaf Springs, taken from the internet at http://www.heathcotes.com/composite-products/composite-leaf-springs/ , 2017, HiP Heathcote Industrial Plastics, United Kingdom.
(Continued)

*Primary Examiner* — Michelle J Lee
*Assistant Examiner* — Daniel A Miller
(74) *Attorney, Agent, or Firm* — Greenberg Traurig, LLP

(57) ABSTRACT

In combination with a knee brace, the variable radius spring assembly of the present invention provides a full range knee orthotic with support to the leg muscles without compromising the range of motion and the patient's normal walk/gate. The assembly comprises upper and lower hinge pieces attached to upper and lower sections of the brace, a spring bracket, and an elongated spring element that extends downward from the upper hinge piece past a catch on the lower hinge piece. Two such assemblies are attached to a knee brace, one on the inner side and one on the outer side. As the lower leg, and the lower hinge piece, move rearward, the catch forces the spring element rearward and slides downward along the spring element. Consequently, the spring
(Continued)

element has a non-linear response requiring approximately the same about of force to deflect the spring element throughout its range of rearward travel.

7 Claims, 10 Drawing Sheets

(58) Field of Classification Search
CPC .... A61H 1/0237; A61H 1/024; A61H 1/0262; A61H 3/00; A61H 2003/005; A61H 1/0214; A63B 21/00; A63B 21/02; A63B 21/04; A63B 21/055; A63B 21/4001; A63B 21/4025
USPC ....... 602/16, 23, 26; 601/5, 84; 482/92, 121, 482/122, 124
See application file for complete search history.

(56) References Cited

U.S. PATENT DOCUMENTS

| | | | |
|---|---|---|---|
| 5,685,525 A | 11/1997 | Oguri et al. | |
| 6,460,240 B1 | 10/2002 | Kielies et al. | |
| 6,471,664 B1* | 10/2002 | Campbell | A61F 5/0123 602/16 |
| 6,612,556 B2 | 9/2003 | Petrina | |
| 6,803,095 B1 | 10/2004 | Halladay et al. | |
| 7,981,495 B2 | 7/2011 | Kim et al. | |
| 8,568,344 B2* | 10/2013 | Ferguson | A61H 3/00 602/16 |
| 8,911,651 B2 | 12/2014 | Muller | |
| 9,180,979 B2 | 11/2015 | Hallander et al. | |
| 9,597,938 B2 | 3/2017 | Spiegel et al. | |
| 9,643,379 B1 | 5/2017 | McKnight et al. | |
| 9,982,734 B2 | 5/2018 | Yoshioka | |
| 10,098,414 B2 | 10/2018 | Cavanagh et al. | |
| 10,189,209 B2 | 1/2019 | Downs et al. | |
| 2002/0072695 A1* | 6/2002 | Doty | A61F 5/0123 602/5 |
| 2004/0153015 A1* | 8/2004 | Seligman | A61F 5/0123 602/16 |
| 2006/0206043 A1* | 9/2006 | Yakimovich | A61F 5/0125 602/5 |
| 2013/0131560 A1* | 5/2013 | Ferguson | A61H 3/00 601/33 |
| 2015/0167768 A1 | 6/2015 | Zhao | |
| 2016/0175134 A1* | 6/2016 | Ghahfarokhi | A61F 5/0127 602/16 |
| 2016/0250094 A1* | 9/2016 | Amundson | A61H 1/0266 623/24 |
| 2017/0122395 A1 | 5/2017 | Kiele et al. | |
| 2017/0259157 A1* | 9/2017 | Stewart | B25J 9/0006 |
| 2018/0055673 A1* | 3/2018 | Humphrey | A61F 5/0125 |
| 2018/0200135 A1* | 7/2018 | Tung | A61H 1/024 |

OTHER PUBLICATIONS

Rahmani, H. et al., "Elastic properties of carbon fibre-reinforced epoxy composites", Polymers & Polymer Composites 23(7):475-481, 2015.

Walck, Christine; "Biomechanical Response of the Knee Complex to a Non-Linear Spring-Loaded Knee Joint Orthosis," Dissertations and Theses, 458 (2019).

* cited by examiner

VARIABLE RADIUS SPRING ASSEMBLY

TECHNICAL FIELD

This invention relates generally to medical devices for anatomical support. This invention relates generally to knee braces. More specifically this invention relates to a variable radius spring assembly for knee braces.

BACKGROUND OF THE INVENTION

Individuals suffering from knee pain, such as from osteoarthritis, or weakened leg muscles often find some relief and support by wearing a knee brace on one or both legs. A conventional knee brace has an upper section and lower bands or sections. The upper section has a front piece that extends around the front of a patient's leg above the knee and is held in place by a removable strap around the back of the leg. The lower section also has a front piece that extends around the front of a patient's leg below the knee and is held in place by a removable strap around the back of the leg. A pair of vertical inner and outer supports adjacent the inner and outer sides of the thigh extend downward from the upper section. A like pair of inner and outer vertical supports adjacent the inner and outer sides of the calf extend upward from the lower section. The two sets of vertical supports are connected to each other with inner and outer hinges that allow the lower section to move along an axis relative to the upper section as the lower leg is bent, such as during walking. The brace is able to stabilize and control motion of the knee. Some braces are used to transfer weight from a weak area of the knee to a stronger area, for example to provide some relief from osteoarthritis.

In the applicant's experience there is a deficiency in the existing and prior art wherein many of the existing braces focus primarily on providing lateral support to the joint rather than provide support and assistance to the leg muscles. One brace provides muscle support, but the device uses a complicated fluid spring system that is expensive and bulky.

In the applicant's experience, there is a need for a knee brace, or a device that can be installed on a knee brace, that will provide both support and assistance to the leg muscles, allowing for a more comfortable walking or running experience. The device of the present invention is believed to accomplish all of the foregoing objectives.

SUMMARY OF THE INVENTION

The present invention provides a new and useful variable radius spring assembly for knee braces. This device is believed to be useful in relieving pain or discomfort in a patient's knee(s), whether caused by osteoarthritis, surgery, or other reasons.

In one of its basic embodiments, the assembly comprises upper and lower hinge pieces, a spring bracket, and an elongated spring element. Two such assemblies are attached to a knee brace, one on the inner side and one on the outer side. In an alternate embodiment only one such assembly may be utilized. For each assembly, the upper and lower hinge pieces are attached to upper and lower sections, respectively, of a knee brace. The spring element is secured to the spring bracket, the spring bracket is secured to the upper hinge piece, and the upper and lower hinge pieces are pivotally connected such that the lower hinge piece rotates relative to the upper hinge piece. The spring element extends downward from the spring bracket past a catch on the lower hinge piece. When the patient on whom the knee brace is secured walks or bends his/her leg at the knee, the lower hinge piece moves rearward with the lower leg and the catch contacts the spring element. As the lower leg, and the lower hinge piece, continue to move rearward, the catch forces the spring element rearward and slides downward along the spring element with a substantially constant force against the spring element. When the leg is extended, the spring element applies a substantially constant force throughout its travel returning to its undeflected state. Consequently, the spring element has a non-linear response and approximately the same amount of force is required to compress the spring element throughout its range of rearward travel while storing the same amount of energy.

When the device is in use it provides a full range knee orthotic that provides support to the leg muscles without compromising the range of motion and the patient's normal walk/gate. Furthermore, the device provides lateral protection and support to the knee joint. The device is ergonomic and robust enough to be worn during activities of daily life and most athletic endeavors.

Thus the present invention provides a new and useful variable radius spring assembly for knee braces. The device of the present invention is believed to accomplish all of the foregoing objectives. Further features and objectives of the present invention will become apparent from the following detailed description and the accompanying drawings.

DETAILED DESCRIPTION OF THE INVENTION

Figure 1:
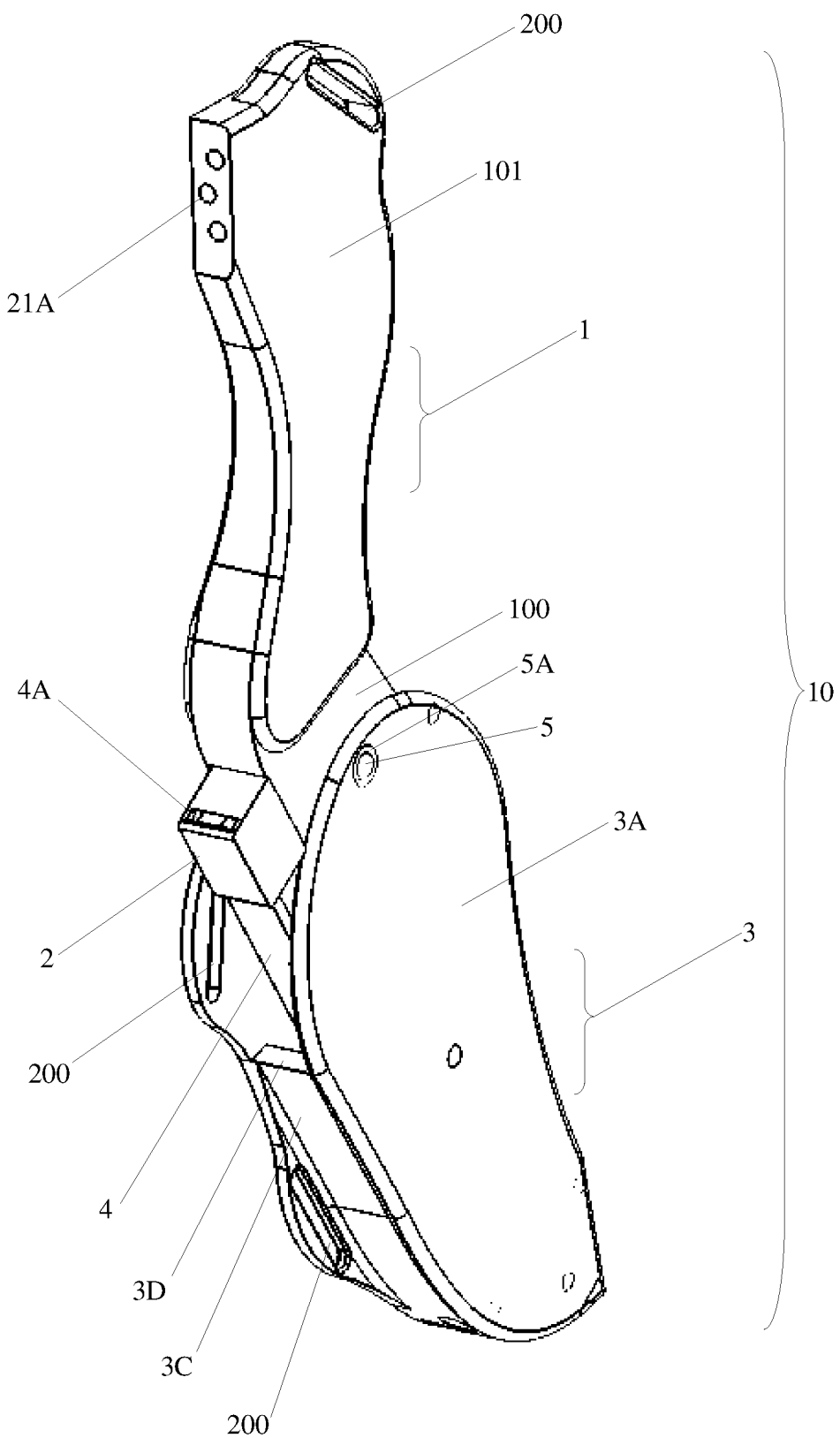
FIG. 1 is an isometric perspective view of a variable radius spring assembly for a knee brace according to the present invention.
Figure 2:
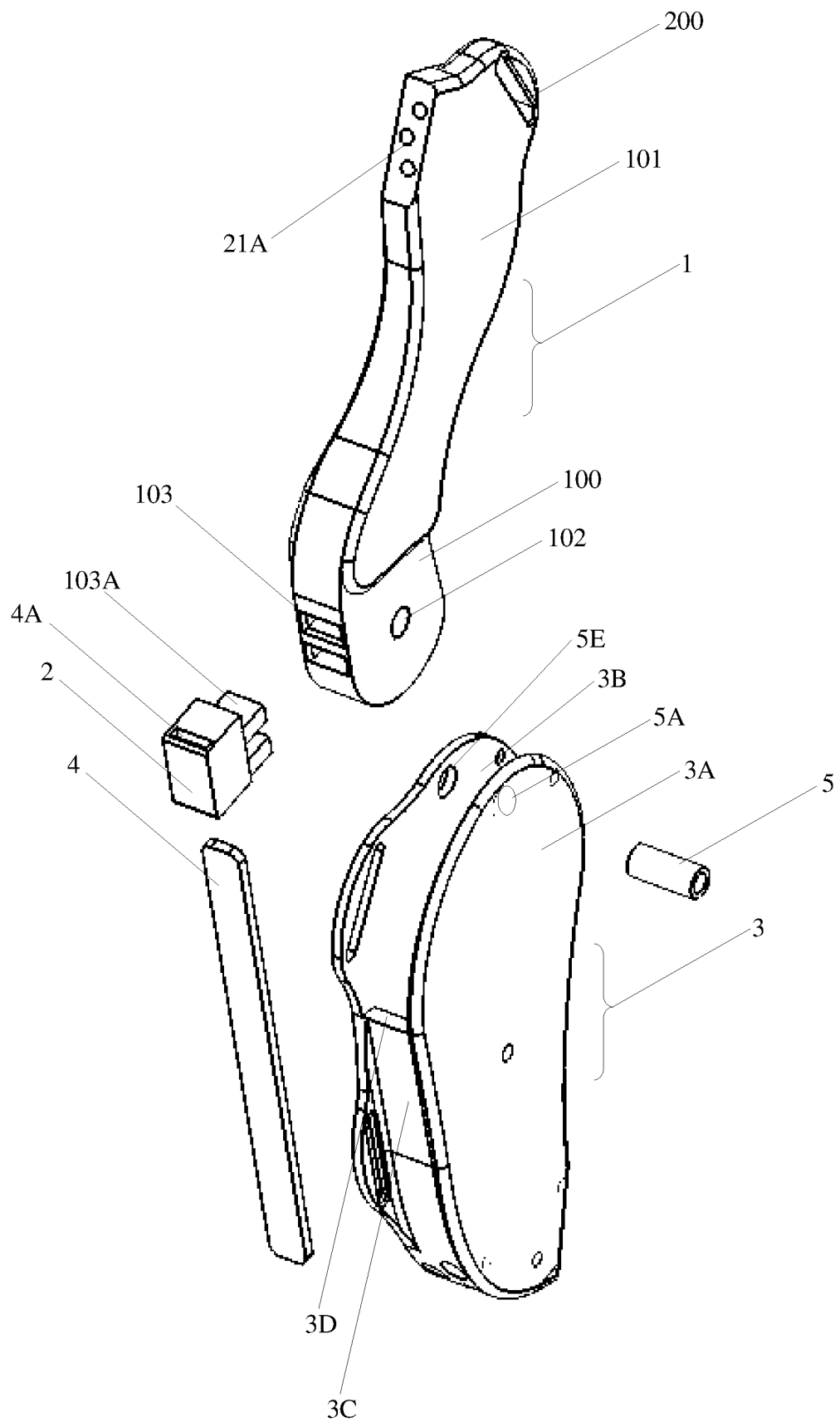
FIG. 2 is an exploded view of the variable radius spring assembly for a knee brace according to the present invention.
Figure 3:
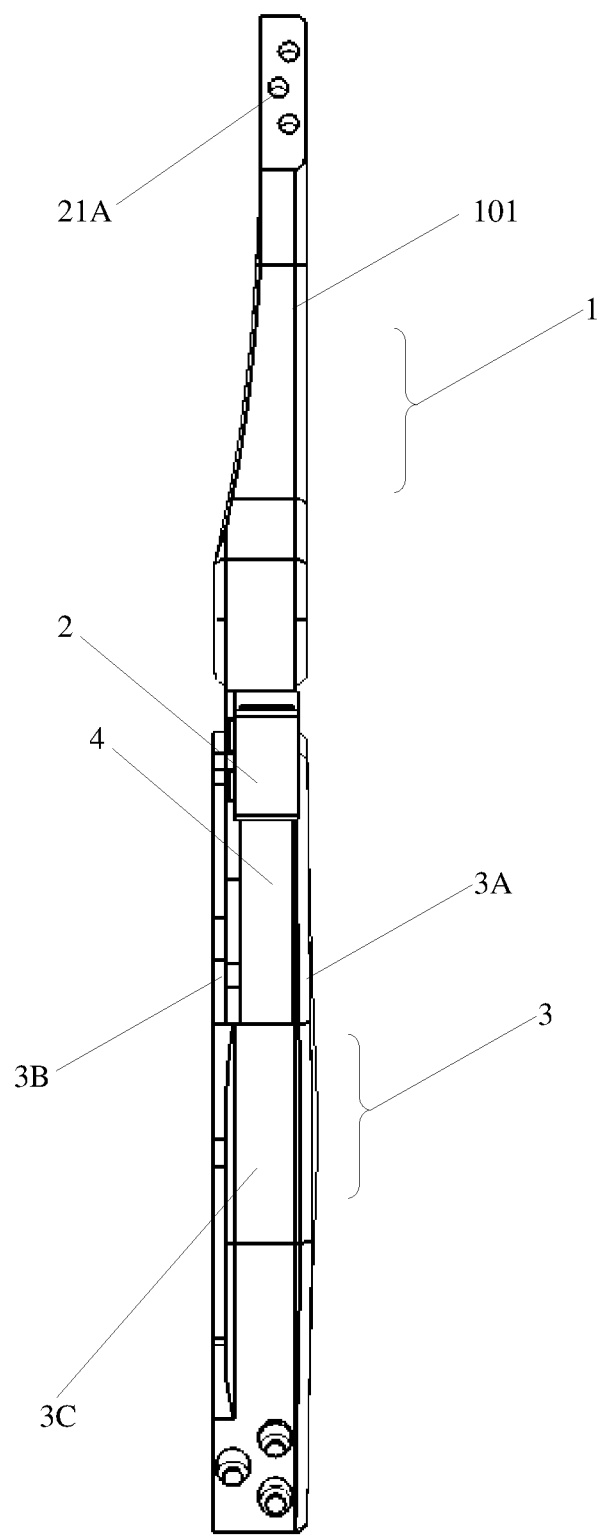
FIG. 3 is a front elevation view of the variable radius spring assembly for a knee brace according to the present invention.
Figure 4:
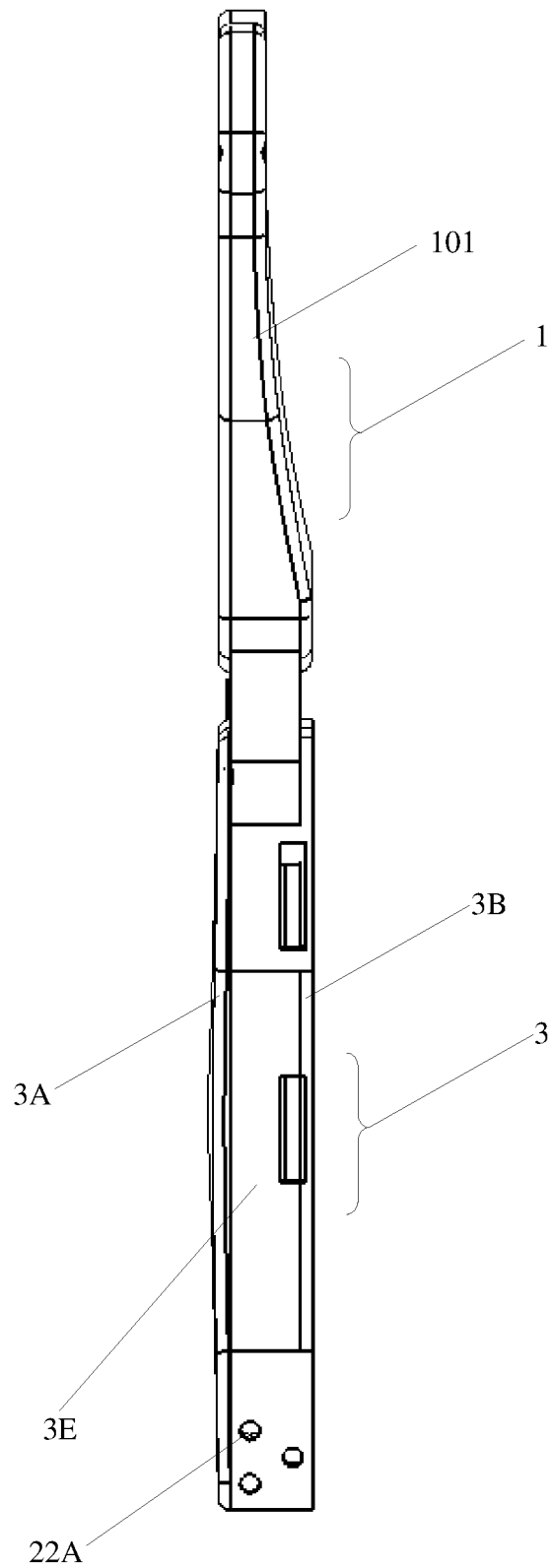
FIG. 4 is a rear elevation view of the variable radius spring assembly for a knee brace according to the present invention.
Figure 5:
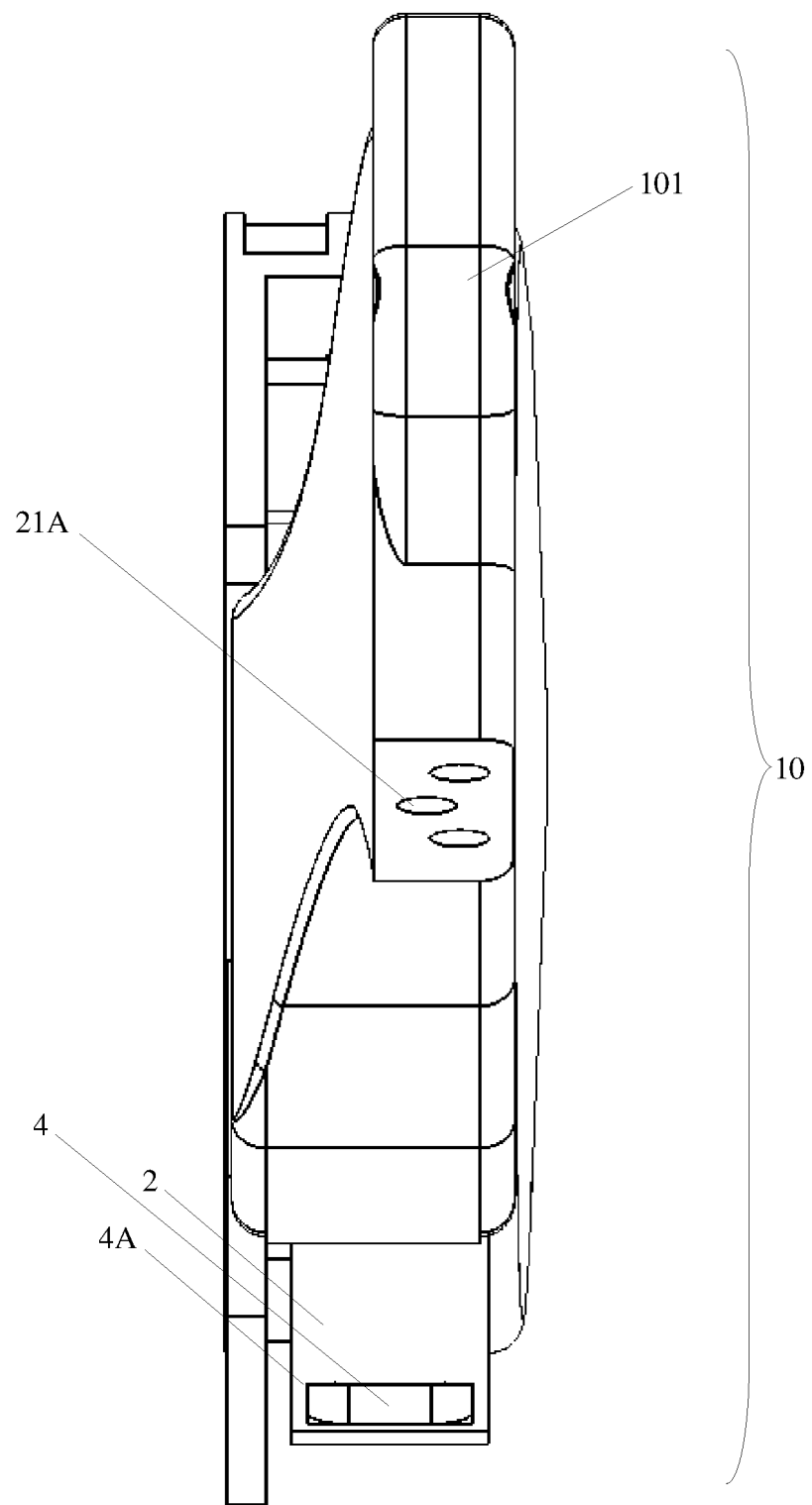
FIG. 5 is a top elevation view of the variable radius spring assembly for a knee brace according to the present invention.
Figure 6:
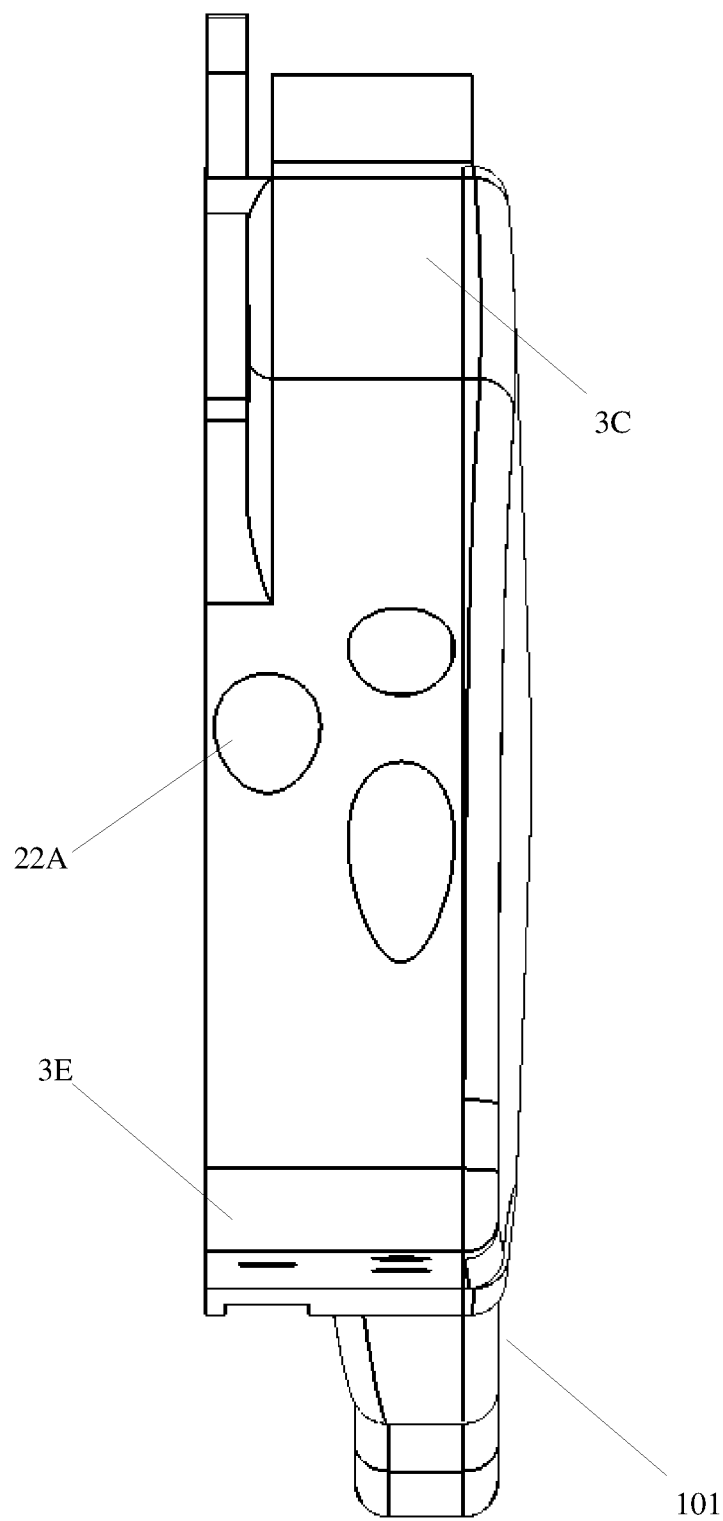
FIG. 6 is a bottom elevation view of the variable radius spring assembly for a knee brace according to the present invention.
Figure 7:
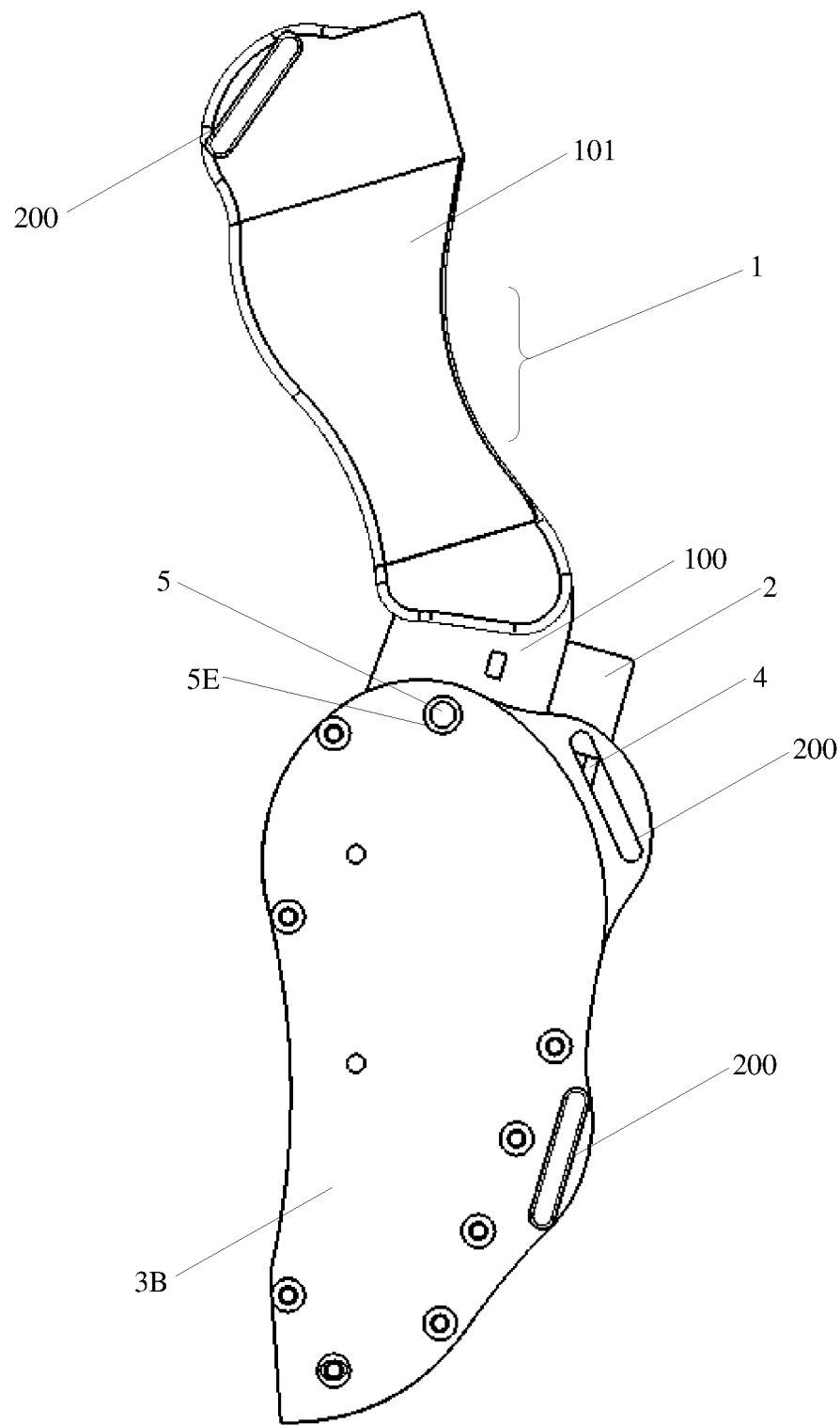
FIG. 7 is a left side elevation view of the variable radius spring assembly for a knee brace according to the present invention.
Figure 8:
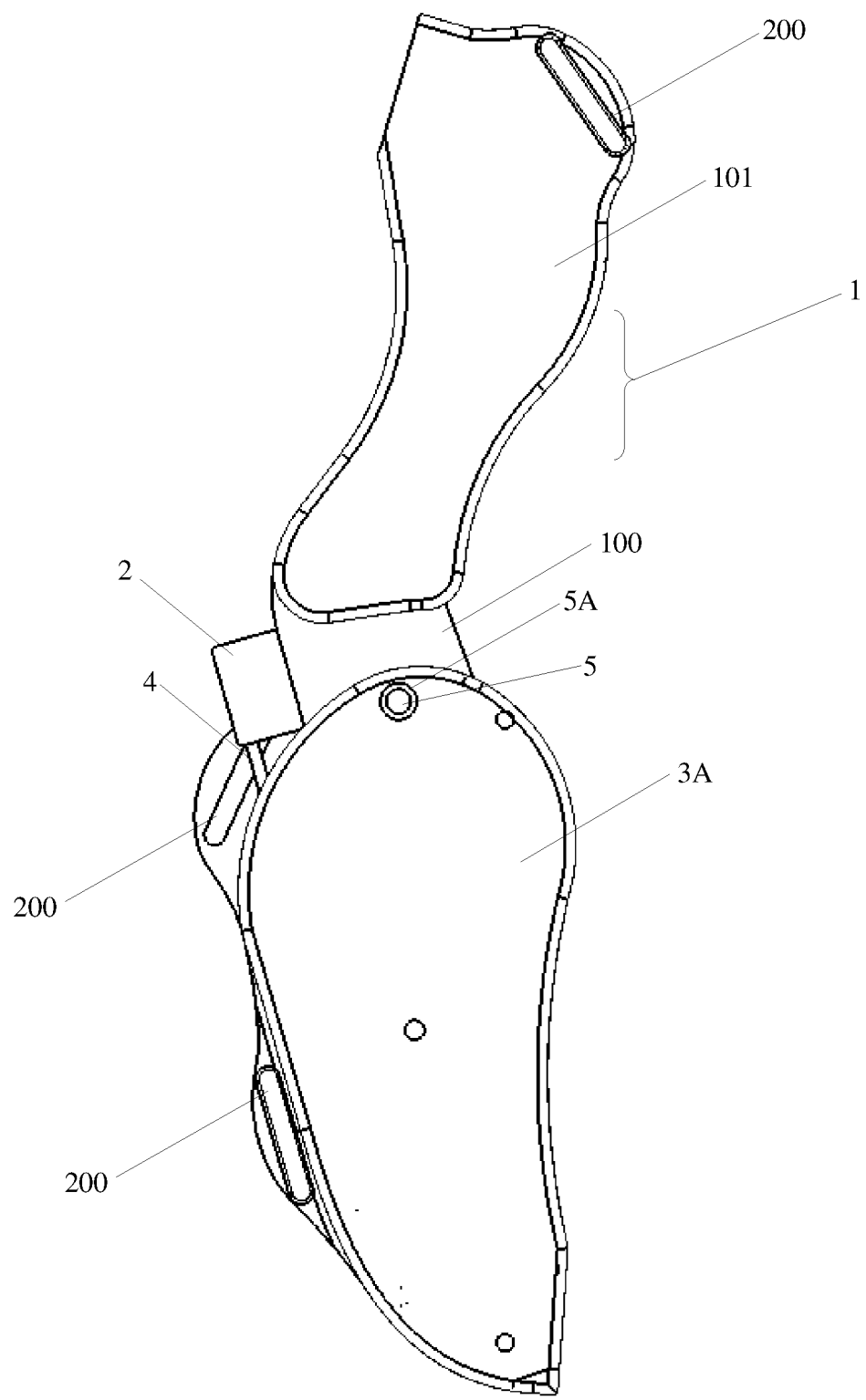
FIG. 8 is a right side elevation view of the variable radius spring assembly for a knee brace according to the present invention.
Figure 9:
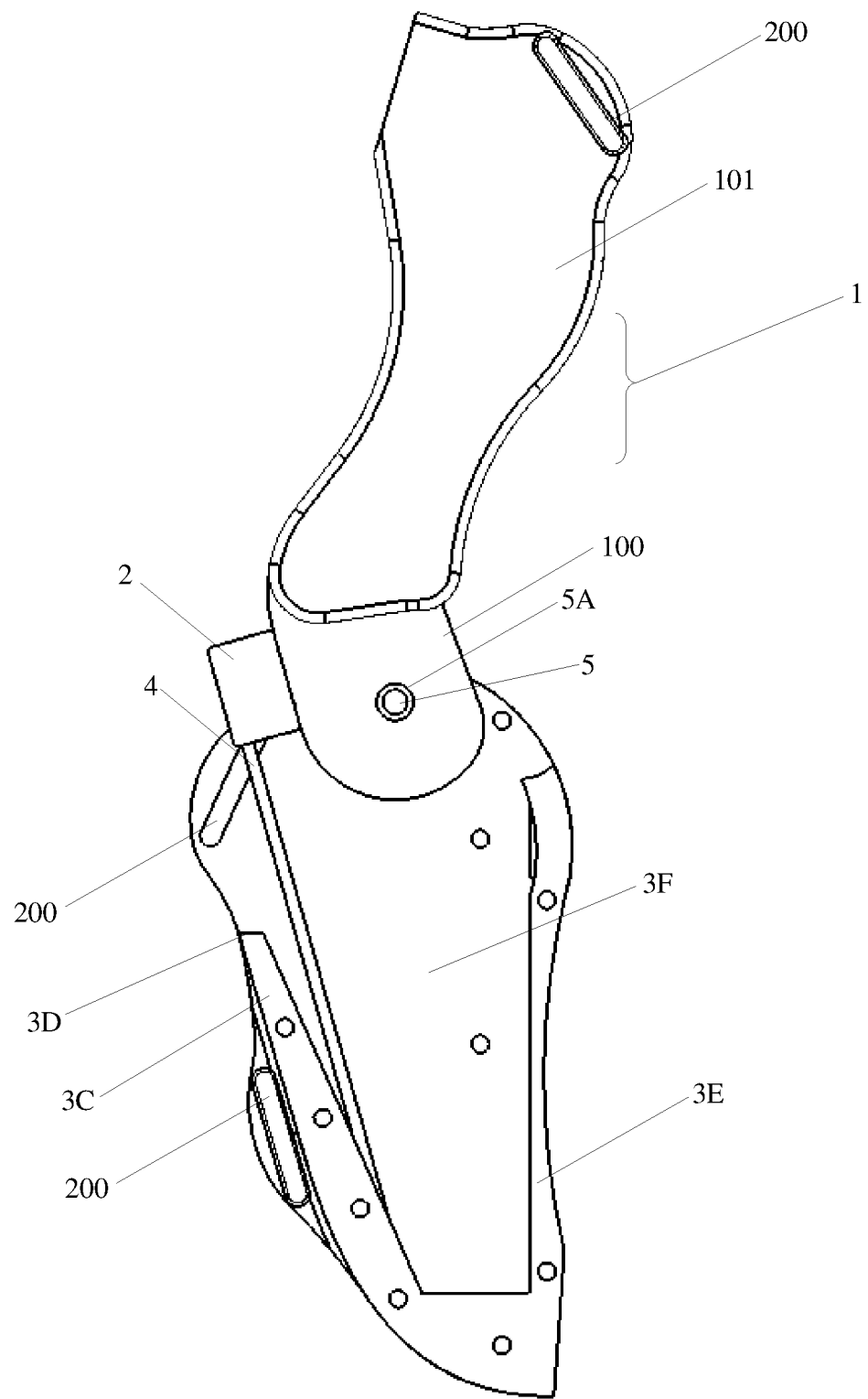
FIG. 9 is a cross-sectional right side view of the variable radius spring assembly for a knee brace according to the present invention.

The present invention provides a new and useful variable radius spring assembly for knee braces. The following description and accompanying drawings disclose at least one version of the device.

Referring now to the invention in more detail in FIG. 1 to FIG. 9 there is a variable radius spring assembly 10 shown generally for knee braces. The assembly 10 comprises an upper hinge piece 1, a spring bracket 2, a lower hinge piece 3, and an elongated spring element 4. The upper hinge piece 1 comprises an upper shaft 101 and a lower cylindrical barrel hinge 100 with a central pivot bore 102 and a spring bracket receiving slot 103 along an anterior aspect of the barrel hinge 100 for receipt of the spring bracket 2 when assembled. The lower hinge piece 3 comprises parallel elongated right and left plates 3A, 3B and a rear plate 3E. The anterior aspect of the lower hinge piece 3 is angled from the middle downward and upward towards the rear. A front plate 3C covers the lower portion of the front. The upper portion of the front, above the upper edge or catch 3D of the front plate 3C, and the top of the lower hinge piece 3 are open thereby creating a void 3F defined by the interior geometry of the surrounding plates 3A, 3B, 3C, 3D and retains the spring element 4 therein when the system is assembled.

The spring bracket 2 is generally prismatic in shape and comprises a slot 4A within which the spring element 4 is secured. The spring element 4 is secured within the slot 4A, and 115 extends downward towards the front plate 3C of the lower hinge piece. When the present invention is assembled the spring element 4 extends into and moves within the void 3F of the lower hinge piece 3. The spring bracket 2 may also be solid. The spring element 4 may also be attached to the spring bracket 2 in other ways or may be attached directly to the upper hinge piece 1. The spring bracket 2 further comprises a plurality of tabs 103A which attach to the spring 120 bracket receiving slot 103 of the upper hinge piece 1.

A bushing, comprising an axle 5 to hold the upper hinge piece 1 and the lower hinge piece 3 together. The axle 5 extends through a right side opening 5A near the top of the lower hinge piece right plate 3A, through the central pivot bore 102 of the barrel hinge 100, and through a left side opening 5E near the top of the left plate 3B of the lower hinge piece 3. The axle is dimensioned such that, when assembled, the upper hinge piece 1, the spring bracket 2, and the lower hinge piece 3 are held together securely while allowing the upper and lower hinge pieces 1, 3 to move freely relative to each other about the axle 5. When the device 10 is assembled, the spring element 4 extends downward through the open front of the lower hinge piece 3 into the interior void 3F of the lower hinge piece 3.

In order to attach the variable radius spring assembly 10 of the present invention to a knee brace, a pair of assemblies 10 are provided. Such a pair of assemblies 10 may have mirrored geometry one to the other. One assembly 10 attaches to the interior aspect of the knee brace medial to the wearer's anatomy, and the other assembly 10 attaches to the exterior aspect of the knee brace radial to the anatomy. Essentially one assembly is on either side of the wearer's knee joint within the brace. In order to attach the assemblies 10 to the brace, a plurality of attaching points 200 present along each assembly 10 for the receipt of attaching means which can be straps, ties, snaps or stitching.

After the pair of devices 10 are attached to the knee brace, the knee brace may be secured to the patient's leg in the usual manner. Once secured, the brace with the devices 10 provides support for the patient's knee. While the following description is made in terms of a single device 10 and its components, it will be appreciated that it applies equally to both of the assemblies 10, which may have mirrored geometry one to the other, attached to the knee brace.

As the patient's lower leg moves backward at the knee, the brace is rotated and the lower hinges 3 of each of the pair of assemblies 10 move backward relative to the upper hinges 1. The upper edge 3D of the front plate 3C of the lower hinge piece 3 contacts the spring element 4 and begins to transfer a load. As the lower leg continues to move farther backward, the front plate 3C presses against the spring hinge 4, causing the spring element 4 to deflect rearward, storing potential energy in the spring element 4 in the form of a bending moment. Due to the kinematics involved, the point at which the load is applied, namely the upper edge catch 3D of the front plate 3 of the lower hinge, travels further away (downward) from the pivoting point or lever fulcrum at the axle 5. This effectively increases the application radius of the lever system, allowing for greater energy storage at relatively the same force as a standard torsion spring.

The upper and lower hinge pieces 1, 3 and the spring bracket 2 may be formed from any appropriate material, such as plastic, composite, or metal, that has sufficient strength to 155 withstand the forces that are placed on them. The spring hinge 4 is preferably formed from a carbon fiber or other like material that can bend sufficiently without breaking and return to its original shape without deformation or memory over time.

Figure 10:
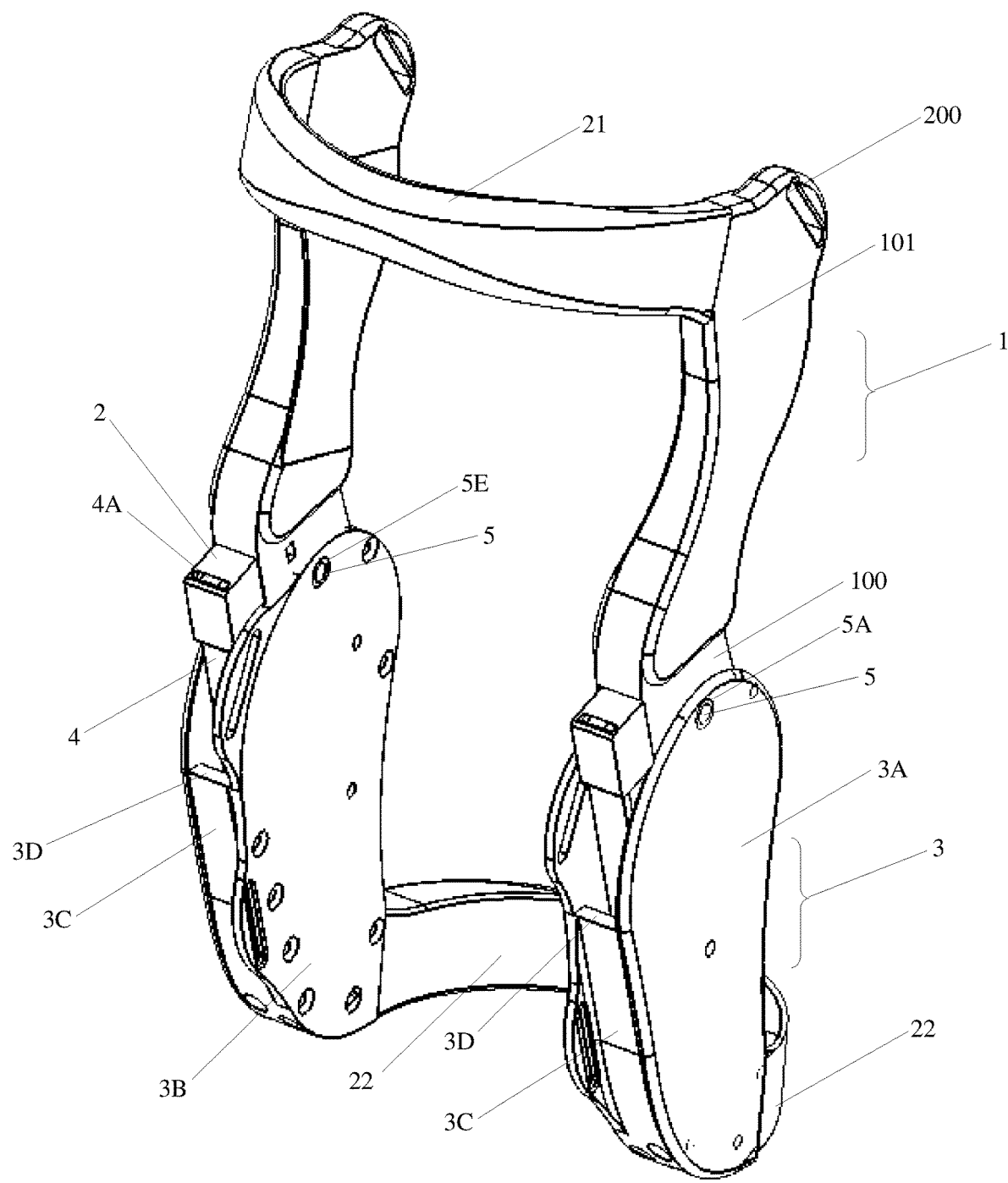
FIG. 10 is a isometric perspective view of an alternate embodiment of the present invention having a pair of variable radius spring assemblies of the present invention.

In an alternate embodiment, the present invention comprises a knee brace 20 having a pair of variable radius spring assemblies 10, as illustrated in FIG. 10. The brace 20 includes an upper frame 21 mechanically connected to an upper aspect of the upper hinge piece 1 of each assembly 10 and a lower frame 22 mechanically connected to a lower aspect of the lower hinge piece 3 of each assembly 10. This embodiment is attached to the patient's anatomy by utilization of the attaching points 200 along the assembly 10. 17. In order to effectuate this configuration in an alternative embodiment of the present invention, the assembly further comprises a plurality of upper frame attaching points 21A for the receipt and attachment of an elongate upper frame 21 to the upper hinge piece 1, and a plurality of lower frame attaching points 22A for the receipt and attachment of an elongate lower frame 22 to the lower hinge piece 3.

A standard linear spring requires more force as the angle of knee flexion increases. When used in a knee brace, a linear spring may provide some support but may also encumber the normal range of motion of the knee and result in unwanted loadings on leg muscles. In contrast with a standard linear spring, the varying radius spring assembly 10 employed by the present invention has a non-linear response. Thus, it requires approximately the same about of force to deflect (compress) the spring element 4 throughout its range of rearward travel while storing the same amount of energy. This provides the same support during extension while requiring less input on compression. When the knee is extended (substantially straight), the assembly 10 provides a counter-balancing force in the direction of extension that inhibits the bending of the knee joint. As a result, weakened leg muscles that may be unable to bear load are supported. As the spring element 4 is deflected during knee flexion, the pickup point, the upper edge catch 3D of the front plate 3C of the lower hinge piece 3, extends, thereby changing the application radius of the moment arm at which the spring element 4 is deflecting allowing the force against it to remain substantially constant. This in turn changes the generated elastic counter force. Similarly, as the leg is extended, the spring element applies a substantially constant force against the upper edge catch 3D of the lower hinge front plate 3C throughout its travel returning to its undeflected state. The magnitude of the counter-balancing force from the assembly 10 can be increased or decreased by altering the cross-sectional area or material composition of the spring element 4 itself.

The previously described versions of the present invention have many advantages including and without limitation, providing support to the leg muscles without compromising the range of motion and the patient's normal walk/gate and providing lateral protection and support to the knee joint. The device is ergonomic and robust enough to be worn during activities of daily life and most athletic endeavors. The device of the present invention is believed to accomplish all of the foregoing objectives. The invention does not require that all the advantageous features and all the advantages need to be incorporated into every embodiment of the invention.

Although the present invention has been described in considerable detail with reference to certain preferred versions thereof, other versions are possible. Therefore the spirit and scope of the appended claims should not be limited to the description of the preferred versions contained therein.

The reader's attention is directed to all papers and documents which are filed concurrently with this specification and which are open to public inspection with this specification, and the contents of all such papers and documents are incorporated herein by reference.

All the features disclosed in this specification may be replaced by alternative features serving the same, equivalent or similar purpose, unless expressly stated otherwise. Thus, unless expressly stated otherwise, each feature disclosed is one example only of a generic series of equivalent or similar features.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. As for "means for" elements, the applicant intends to encompass within the language any structure presently existing or developed in the future that performs the same function. The invention should therefore not be limited by the above described embodiment, method, and examples, but by all embodiments and methods within the scope and spirit of the invention.

What is claimed is:

1. A knee brace comprising:
   (a) an upper frame portion, wherein the upper frame portion is configured to engage a portion of a human leg above a knee;
   (b) a lower frame portion, wherein the lower frame portion is configured to engage a portion of the human leg below the knee;
   (c) an upper hinge portion having a first end and a second end opposite the first end, wherein the first end of the upper hinge portion is attached to the upper frame portion;
   (d) a lower hinge portion having a first end and a second end opposite the first end, wherein the second end of the lower portion is attached to the lower frame portion;
      wherein the first end of the lower hinge portion is connected to the second end of the upper hinge portion via an axle;
      wherein the lower hinge portion comprises:
         a left plate and a right plate oriented parallel to each other;
         a front plate extending from the left plate to the right plate and located between the left plate and the right plate;
         a rear plate extending from the left plate to the right plate and located between the left plate and the right plate;
            wherein the left plate, the right plate, the front plate, and the rear plate define an open prismatic box having a void therein;
         wherein the upper hinge portion is disposed between the left plate and the right plate;
   (e) a spring bracket attached to the upper hinge portion, wherein the spring bracket is attached to the second end of the upper hinge portion,
      wherein the spring bracket comprises:
         an elongate linear spring element;
            wherein the elongate linear spring element is attached to the upper hinge portion;
            wherein the elongate linear spring element is not attached to the lower hinge portion;
   (f) a catch located on the lower hinge portion;
   wherein the front plate is sloped so that in a first position, the elongate linear spring element is spaced away from the catch, and the front plate engages the elongate linear spring element when the lower frame portion moves from the first position to a second bent position, thereby creating a fulcrum;
   wherein, the lower frame portion is configured to move from the first position to the second bent position about the axle as a user bends its knee;
   wherein the catch forces the elongate linear spring element rearward and slides downward along the elongate linear spring element with a substantially constant force against the elongate linear spring element;
   wherein the lower frame portion is configured to return from the second bent position to the first position about the axle as the user extends its leg;
   wherein the elongate linear spring element is configured to apply the constant force throughout the movement of the lower frame portion from the second bent position to the first position;
   wherein the upper hinge portion, the lower hinge portion, the spring bracket, and the elongate linear spring element are configured to be disposed on a lateral side of the knee.

2. The knee brace of claim 1, wherein the upper hinge portion comprises at least one attachment point; and
   wherein the knee brace comprises a strap connected to the attachment point, and wherein the strap is configured to engage the leg of the user above the knee to secure the knee brace to the leg of the user.

3. The knee brace of claim 2, wherein the lower hinge portion comprises another attachment point; and
   wherein the knee brace comprises a second strap connected to the another attachment point, and wherein the strap is configured to engage the leg of the user below the knee to secure the knee brace to the leg of the user.

4. The knee brace of claim 1, wherein the upper hinge portion comprises at least one slot, wherein the spring bracket comprises at least one tab, and wherein the tab is adapted to be secured within the slot, thereby attaching the spring bracket to the upper hinge portion.

5. The knee brace of claim 1, wherein the elongate linear spring element is a carbon fiber spring element.

6. The knee brace of claim 1, wherein a lower portion of the elongate linear spring element is configured to move within the prismatic box of the lower hinge portion during movement of the lower frame portion from the first position to the second bent position.

7. The knee brace of claim 1, wherein the front plate as sloped is configured to provide a wider angle of contact between the catch and the elongate linear spring element.

* * * * *